(12) United States Patent
Karch et al.

(10) Patent No.: US 11,925,514 B2
(45) Date of Patent: Mar. 12, 2024

(54) APPARATUS AND METHODS FOR INTRAOPERATIVE SURGICAL INSTRUMENT STERILIZATION

(71) Applicant: KMW Enterprises LLC, Crowley Lake, CA (US)

(72) Inventors: Michael Karch, Mammoth Lakes, CA (US); Meredith Moss, Crowley Lake, CA (US); Chris Wylie, San Antonio, TX (US)

(73) Assignee: KMW ENTERPRISES LLC, Crowley Lake, CA (US)

( * ) Notice: Subject to any disclaimer, the term of this patent is extended or adjusted under 35 U.S.C. 154(b) by 314 days.

(21) Appl. No.: 16/862,438

(22) Filed: Apr. 29, 2020

(65) Prior Publication Data

US 2020/0337800 A1    Oct. 29, 2020

Related U.S. Application Data

(60) Provisional application No. 62/840,282, filed on Apr. 29, 2019.

(51) Int. Cl.
*A61B 90/70*    (2016.01)
*A61L 2/10*    (2006.01)
(Continued)

(52) U.S. Cl.
CPC ............... *A61B 90/70* (2016.02); *A61L 2/10* (2013.01); *A61L 2/18* (2013.01); *A61L 2/26* (2013.01);
(Continued)

(58) Field of Classification Search
CPC . A61B 90/70; A61L 2/26; A61L 2/025; B08B 3/08; B08B 3/12
See application file for complete search history.

(56) References Cited

U.S. PATENT DOCUMENTS

| 4,448,750 A | 5/1984 | Fuesting |
| 6,468,953 B1 | 10/2002 | Hitchens |

(Continued)

FOREIGN PATENT DOCUMENTS

| CN | 203898777 | 10/2014 |
| CN | 206315305 | 7/2017 |

(Continued)

*Primary Examiner* — Natasha N Campbell
(74) *Attorney, Agent, or Firm* — Dunn DeSantis Walt & Kendrick LLP; Joshua Emory

(57) ABSTRACT

The present invention relates to apparatus and methods for cleaning, decontaminating, and/or sterilizing an instrument during the intraoperative phase of a surgical procedure. In exemplary embodiments, the apparatus comprises: a container having an aperture, a bottom portion, and at least one sidewall defining an instrument bath configured to hold a cleaning agent; a vibration means and radiation means coupled to the container; and a power supply. It is contemplated that at least one of the sidewalls of the container comprises a longitudinal channel disposed within the sidewall for housing the radiation means. It is further contemplated that the cleaning agent can comprise an aqueous solution of chlorhexidine, that the radiation means is configured to emit ultraviolet radiation in a range of at least 100 nanometers to 400 nanometers, and that the vibration means is configured to emit ultrasonic radiation in a range of at least 20 kilohertz to 120 kilohertz.

16 Claims, 5 Drawing Sheets

(51) Int. Cl.
*A61L 2/18* (2006.01)
*A61L 2/26* (2006.01)
*B08B 3/08* (2006.01)
*B08B 3/12* (2006.01)

(52) U.S. Cl.
CPC ............... *B08B 3/08* (2013.01); *B08B 3/12* (2013.01); *A61L 2202/122* (2013.01); *A61L 2202/14* (2013.01); *A61L 2202/17* (2013.01); *A61L 2202/24* (2013.01)

(56) References Cited

U.S. PATENT DOCUMENTS

| | | |
|---|---|---|
| 6,605,252 B2 | 8/2003 | Omasa |
| 6,858,181 B2 | 2/2005 | Aoyagi |
| 7,217,358 B2 | 5/2007 | Evans |
| 7,393,818 B2 | 7/2008 | McDonnell et al. |
| 7,718,122 B2 | 5/2010 | Smith et al. |
| 8,007,819 B2 | 8/2011 | Shaheen et al. |
| 8,241,258 B2 | 8/2012 | Pelkus |
| 8,507,875 B2 | 8/2013 | Kobayashi et al. |
| 8,697,140 B2 | 4/2014 | Arndt et al. |
| 9,622,481 B2 | 4/2017 | Gawande et al. |
| 10,028,637 B2 | 7/2018 | Ju |
| 2002/0159917 A1 | 10/2002 | Swart et al. |
| 2005/0147526 A1 | 7/2005 | Hishida |
| 2005/0220665 A1 | 10/2005 | Ding |
| 2008/0289971 A1 | 11/2008 | Shigihara et al. |
| 2010/0132111 A1 | 6/2010 | Na |
| 2013/0037047 A1 | 2/2013 | Saiger |
| 2013/0098408 A1 | 4/2013 | Tanaka et al. |
| 2013/0186429 A1* | 7/2013 | Morita ............... A61L 2/20 134/1 |
| 2017/0100498 A1 | 4/2017 | Sobhy et al. |
| 2019/0223978 A1* | 7/2019 | Graves ............... A61B 90/70 |
| 2020/0002647 A1* | 1/2020 | Farvid ............... C11D 11/0094 |
| 2021/0015307 A1* | 1/2021 | Oberholzer ............... E03C 1/18 |

FOREIGN PATENT DOCUMENTS

| | | | | |
|---|---|---|---|---|
| CN | 206716604 | | 12/2017 | |
| CN | 108480310 | | 9/2018 | |
| EP | 0286524 | | 10/1988 | |
| GB | 2040150 A | * | 8/1980 | ............ A61L 2/025 |
| JP | 2000217781 A | * | 8/2000 | |
| JP | 2007082900 A | * | 4/2007 | |
| KR | 20060103609 A | * | 10/2006 | |

* cited by examiner

APPARATUS AND METHODS FOR INTRAOPERATIVE SURGICAL INSTRUMENT STERILIZATION

CROSS-REFERENCE TO RELATED APPLICATIONS

This application claims priority to U.S. Provisional Application Ser. No. 62/840,282, filed on Apr. 29, 2019 and entitled "Apparatus, Systems, and Methods for Introperative Decontamination of Surgical Instruments," which is incorporated herein by reference in its entirety.

FIELD OF THE INVENTION

The present invention relates to apparatus and methods for using an surgical instrument sterilization device that utilizes multiple modalities to clean, disinfect and/or sterilize surgical instruments exposed to bodily fluids and/or tissues during the intraoperative phase of a surgical procedure.

BACKGROUND OF THE INVENTION

It is estimated that the number of shoulder, hip, and knee replacement surgeries will increase by 100%, 200% and 600%, respectively by the year 2030 due to our aging population, more active lifestyles and longer expected lifespans. These surgeries are among the most expensive of all surgical procedures due to their increased technical complexity, aged patient comorbidities, the time required for the procedure, and rising implant costs. Significant oversight, regulation, and pressure are being exerted on surgeons and hospital systems to reduce the cost of joint replacement surgeries and their associated complications.

Joint replacement surgeries come in two basic categories, primary joint replacement and revision joint replacement. Primary joint replacement surgery involves replacing a native shoulder, hip or knee joint with a prosthetic one that contains a combination of metallic, ceramic and/or plastic components. Revision replacement surgery involves removing a previously placed (and now failed) prosthetic and revising it to a new one.

Prosthetic devices fail, are removed, and/or are replaced/revised for a number of reasons including: age, aseptic or non-infectious loosening of the bone/implant or bone/cement/implant interface, septic loosening due to infection, trauma causing fracture of the bone around the implant and subsequent prosthetic loosening and/or dislocation of the prosthetic components. Prosthetic joint infections are among the most devastating and costliest reasons for revision surgery in terms of morbidity, mortality, treatment costs and patient down time. Patient morbidity, lost work, and loss of life are significant with prosthetic joint infections. The survival rate at one year for a prosthetic joint infection is worse than several known cancer diagnoses, including Testicular, Hodgkin's Lymphoma, Melanoma and Breast cancer.

Bacteria have an affinity for large metal implants. Bacterial infections occur at an expected rate of approximately 1-2% for primary joint replacement surgeries and 3-13% for revision joint replacement surgeries. Many risk factors have been identified as potential causes of these bacterial infections including poor host defenses, (comorbidities including obesity, smoking, alcohol use, diabetes, etc.), the quality of the patient's skin coverage and the microcirculation of soft tissues, breaches in surgical technique, poor patient hygiene, complexity of the surgical procedure, and importantly, length of the surgical procedure. Primary hip and knee replacement surgeries typically take between 45 to 120 minutes (with an average of 60 minutes) to complete, while average revision surgeries typically last twice as long.

With regards to surgical procedure length, it is known that bacteria grow exponentially over time and that instruments used at the beginning of the procedure may become contaminated in a variety of ways, including by: (1) the patient's own skin bacterial flora, (2) ambient bacteria in the operating room suite, (3) incomplete or imperfect filtering of ambient air in the operating room, (4) operating room personnel, (5) sterile dressed (scrubbed, gowned, gloved and masked) operating room personnel coming into and out of the operating room, and (6) non-sterile dressed sales representatives and other third parties entering and exiting the operating room suite. Over the length of a surgical procedure, the blood and organic tissue on used surgical instruments creates the perfect culture media for bacteria to grow.

It is estimated that a single prosthetic joint infection will cost the U.S. health care system between $60,000 and $220,000, excluding patient loss of work/revenue, disability compensation, legal fees, court awarded damages, and insurance premiums paid by surgeons and hospitals. Prosthetic joint infections are one of the leading causes of malpractice litigation against orthopaedic surgeons and the health care institutions they work for. Despite the fact that prosthetic joint infections occur with statistical predictability, insurance companies have deemed them to be a "never event" in terms of triggering insurance coverage, which shifts the blame for prosthetic joint infections to the physician, hospital, and healthcare system at large.

Both hospitals and individual physicians are being judged and ranked based on their "value" rather than "volume," where "value" is defined as outcome divided by cost. Given the statistical occurrence of a prosthetic joint infection, this represents a significant decrease in the described "value." As such, many smaller to mid-size healthcare institutions are dissuading their surgeons from performing revision joint replacement surgeries. Whereas, larger healthcare institutions that continue to perform revision joint replacement surgeries, sustain a heavier burden of those surgeries, a higher infection rate, lost "value," diminished reputation, decreased insurance coverage, increased litigation, and lost revenue. Insurance policies are being granted or denied based on how much "value" a physician or hospital system can bring to the table. Given the statistical occurrence of prosthetic joint infections, the ubiquitous nature of bacteria, and uncontrollable patient risk variables, prosthetic joint infections are impossible to eradicate.

In standard practice, surgical instruments are sterilized prior to the start of a procedure (i.e. preoperative phase) and/or re-sterilized after the end of the procedure (i.e. postoperative phase). However, presently, surgical instruments that are used at the beginning or middle of a surgical procedure are routinely used minutes to hours later in the same procedure without being re-sterilized. Instruments that were completely sterile at the beginning of a procedure become contaminated during the procedure with a patient's own blood, organic tissue, and/or skin bacteria flora. These contaminated instruments are repeatedly moved between the back table and the surgical site. Multiple studies have shown positive bacterial cultures on surgical instruments that increase with time. As such, instrument sterility decreases with each passing minute of a surgical procedure.

It is believed that most surgical site infections occur as a result of using surgical instruments that have been contaminated with the patient's own skin bacteria flora. Surgical instruments that are used at the beginning of a procedure and reused later in the procedure can inoculate bacteria within the surgical site and be the source of prosthetic joint infection. However, due to cost, space limitations, as well as other inefficiencies, it is impractical to use surgical instruments only once during a procedure and replace them with new sterilized instruments. Sadly, a one hundred percent 3σ bacteria kill rate and absolute instrument sterility has never been achieved. Despite adherence to strict hand washing protocols, sterile technique, instrument bio-decontamination, personal space suits, laminar and negative air flow exchanges, surgical site infections still exist. Various strategies that have been developed to decrease the risk of bacterial infections associated with surgical instruments.

Although in some operating rooms, surgical instruments are soaked in a surgical basin with chlorohexidine, this is not considered a national standard. Chlorohexidine can produce a bacteria kill rate of 99.8% if used correctly, including soaking instruments for a minimum of three minutes. But surgical instruments that are soaked in chlorohexidine rarely, if ever, are completely submerged for the required time. And, the reality is that most contaminated surgical instruments sit on tables in piles open to surrounding sources of contamination. When these instruments are reused later in the procedure, they contaminate the surgical wound near the prosthetic implant.

Use of negative pressure and laminar air flow systems have been established as a standard in operating rooms in the United States to decrease bacterial counts. These air exchange systems decrease bacterial counts within the air that could potentially contaminate the surgical wound or instruments. Within the context of a laminar air flow system, the surgical field is theoretically the most sterile, while the peripheral air is less and less sterile the more one moves away from the center of the laminar air flow. Instrument basins with chlorohexidine are typically placed at the periphery of the laminar flow track. As such, these instrument basins are theoretically less sterile than ones placed at the center of the laminar flow track, and are more subject to skin and hair slough from non-sterile, non-scrubbed individuals present in the operating room.

Ultraviolet ("UV") light has been used in operating rooms to kill bacteria on the skin, within the surgical wound, and in the air around the surgical field. Although highly effective, UV technology has not been popularized for use in the operating room because individuals working in close proximity to such technology are subjected to increased health risks, including cornea damage, retinal burns, cataracts, and/or skin cancer.

Strategies exist for diminishing the potential harm from using UV radiation in the operating room setting. Operating room personnel can wear protective eye gear that is bulky and limits the acute vision needed to see and operate on delicate tissues. But, for this reason alone, many surgeons refuse to accept and use UV technology. The UV light source can also be moved further away from the eyes of the operating room personnel. But this option is less effective in killing bacteria because the effectiveness of UV light diminishes as the distance from the intended target increases. Although UV is effective in reducing bacterial counts in the operating room, the aforementioned problems have decreased the acceptance of UV light technology in the operating room. Additionally, selection of specific UV wavelengths can reduce its potential harm on operating room personnel. See e.g., Buonanno et al, Germicidal Efficacy and Mammalian Skin Safety of 222-nm UV Light, 2017 April, Radiat Res., 187(4):483-491 (A range of UV wavelengths, specifically between 200 and 222 nm is equitoxic to bacteria as typical germicidal lamps emitting light at 254 nm, but without associated skin damage risks). Thus, UV technology can be an effective tool against combating surgical site infections.

Further, a combination of more than one sterilization strategy has been employed for sterilizing surgical instruments during the preoperative and/or postoperative phase of a surgical procedure. For example, U.S. Pat. No. 4,448,750, Fuesting, filed May 23, 1984, entitled "Sterilization Method," discloses sterilization of instruments by use of disinfectants (aqueous Solution of Sodium Dodecyl Sulfate and Carbamide), ultrasonic radiation, and UV light. U.S. Pat. No. 685,818, Aoyagi, filed Jan. 21, 2003, entitled "Method for Cleaning and Sterilizing Medical Equipment After Use", discloses a method for the sterilization of instruments using a combination of chlorine dioxide solution or gas and ultrasonic cleaning. United States Patent Publication No. 2002/0159917, Swart et al., published Oct. 31, 2002, entitled "System and Method for Cleaning, High Level Disinfection, or Sterilization of Medical or Dental Instruments or Devices," discloses sterilizing instruments with a cleaning solution, sonicator, and UV light. United States Patent Publication No. 2005/0220665 Ding, published Oct. 6, 2005, entitled "Low Temperature Sterilization and Disinfections Method and Apparatus for Medical Apparatus and Instruments," discloses sterilizing instruments with a disinfecting bath, ultrasound generator and UV light. United States Patent Publication No 2013/0037047, Saiger, published Feb. 14, 2013, entitled "Method for Machine Cleaning and Disinfecting Objects," discloses sterilizing instruments with a cleaning solution, ultrasonicator, and UV light. United States Patent Publication No. 2017/0100498, Sobhy et al., published Apr. 13, 2017, entitled "Disinfecting Apparatus," discloses sterilizing instruments with a disinfecting solution and UV light. European Patent Publication No. 0286524, Lerner et al., published Dec. 10, 1988, entitled "Method and Apparatus for Disinfecting Instruments," discloses sterilizing instruments within a liquid solution, ultrasonic radiation, and UV light. China Patent Publication No. 206716604, Ling et al., published Aug. 12, 2017, entitled "Medical Instrument Circulating Perfusate Belt Cleaning Device," discloses sterilizing instruments with a cleaning solution, ultrasonic generator, and UV light. China Patent Publication No. 20615305, Ning et al., published Nov. 7, 2017, entitled "Medical Instrument Cleaning and Disinfecting Case," discloses sterilizing instruments within a closed box using a cleaning solution, ultrasonic generator and UV light. However, each of these references suffer from one or more disadvantages, including, but not limited to, the inability to use such devices during the intraoperative phase of a surgical procedure because they are large and bulky, very costly to manufacture, non-mobile, cannot be used in simultaneous cases, and/or are located outside the operating suite in common decontamination areas.

The above prior art references to Fuesting, Aoyagi, Swart, Ding, Saiger, Sobhy, Lerner, Ling and Ning and all other extraneous materials discussed herein are incorporated herein by reference in their entirety. Where a definition or use of a term in an incorporated reference is inconsistent or contrary to the definition of that term provided herein, the definition of the term provided herein applies and the definition of that term in the reference does not apply.

Based on the foregoing, improved apparatus and methods for cleaning, disinfecting and/or sterilizing surgical instruments in real-time during the intraoperative phase of a surgical procedure are greatly needed, including apparatus and methods that are cost effective, disposable, and that can employ a combination of sterilization strategies, including use of anti-bacterial agents, UV light, and ultrasonic vibration.

SUMMARY OF THE INVENTION

In a first aspect of the invention, an apparatus for cleaning, decontaminating, and/or sterilizing an instrument during an intraoperative phase of a surgical procedure is disclosed. In one embodiment, the apparatus comprises: a container having an aperture, a bottom portion, and at least one sidewall defining a bath configured to hold a cleaning agent; a vibration means coupled to the container; a radiation means coupled to the container; and a power supply. In one variant, the cleaning agent comprises an aqueous solution of chlorohexidine, the radiation means is configured to emit ultraviolet radiation in a range of at least 100 nanometers to 400 nanometers, and the vibration means is configured to emit ultrasonic radiation in a range of at least 20 kilohertz to 120 kilohertz. In further variants, the apparatus and/or container can be disposable, utilize modular components, and/or be further configured to be utilized in conjunction with a disposable liner insert. In additional variants, the cleaning agent can be prepackaged within the container in disposable fashion.

In a second aspect of the invention, an apparatus for cleaning, decontaminating, and/or sterilizing an instrument during an intraoperative phase of a surgical procedure is disclosed. In one embodiment, the apparatus comprises: a disposable container having an aperture, a bottom portion, and at least one sidewall defining a bath configured to hold a cleaning agent; a vibration means coupled to the container; a radiation means coupled to the container; and a power supply; wherein the at least one sidewall further comprises a longitudinal channel disposed within the at least one sidewall and configured to have an operational angle of between 15 to 50 degrees relative to the bottom portion, and wherein the radiation means is disposed within the longitudinal channel. In one variant, the longitudinal channel further comprises a shrouded lip portion. In further variants, the vibration means and radiation means can be molded within the container.

In a third aspect of the invention, a method for cleaning, decontaminating, and/or sterilizing an instrument during the intraoperative phase is disclosed. In one embodiment, the method comprises: immersing the instrument in an apparatus for cleaning, decontaminating and/or sterilizing the instrument during an intraoperative phase of a surgical procedure, wherein the apparatus comprises a container having an aperture, a bottom portion, and at least one sidewall defining a bath configured to hold a cleaning agent; immersing the instrument within the cleaning agent disposed within the bath of the container; exposing the instrument while immersed in the cleaning agent to an ultrasonic radiation emitted from a vibration means coupled to the container; and exposing the instrument while immersed in the cleaning agent to ultraviolet radiation emitted from one or more radiation means coupled to the container; wherein the steps of utilizing the apparatus, immersing the instrument within the cleaning agent, exposing the instrument to ultrasonic radiation, and exposing the instrument to ultraviolet radiation are simultaneously performed during the intraoperative phase of the surgical procedure.

Other features and advantages of the present invention will immediately be recognized by persons of ordinary skill in the art with reference to the accompanying drawings and detailed description of exemplary embodiments as discussed herein.

BRIEF DESCRIPTION OF THE DRAWINGS

The accompanying drawings illustrate various aspects and embodiments of the present invention disclosed herein, but should not be construed as restricting the scope of the invention in any manner. In the drawings, like reference numerals refer to the same or similar elements or components.

DETAILED DESCRIPTION OF THE INVENTION

Various aspects and embodiments of the apparatus and methods of the present invention are now described in detail. Reference is made to the drawings, wherein like numerals refer to the same or similar parts throughout. The present invention is intended for intraoperative sterilization of surgical instruments in all surgical procedures, including, but not limited to, cardiac, thoracic, general surgical, plastic, ENT, OBGYN, urological and dental procedures. Although the apparatus and methods of the present invention are described primarily with respect to sterilization of instruments for surgical procedures, the present invention may be readily adapted to nonsurgical environments as well, Hence, a myriad of other applications of the present invention are contemplated.

Exemplary Apparatus

Figure 1:
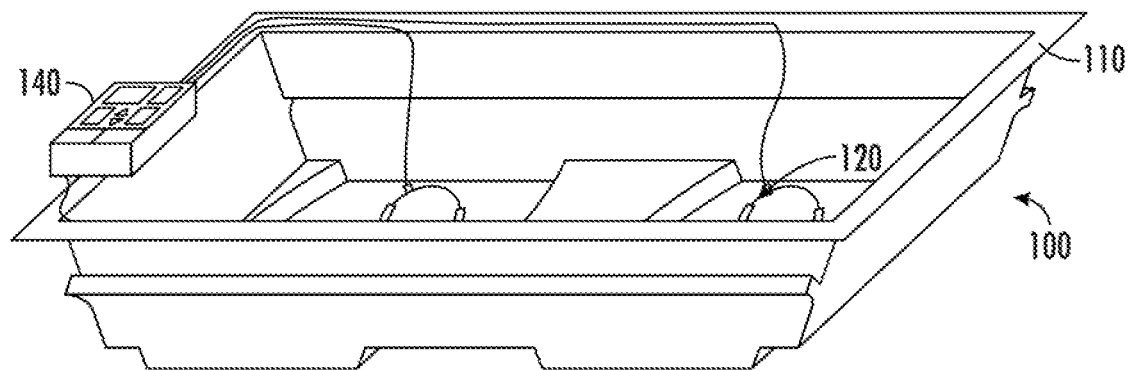
FIG. 1 is a perspective view illustrating an embodiment of an intraoperative sterilization apparatus according to the present invention.
Figure 2:
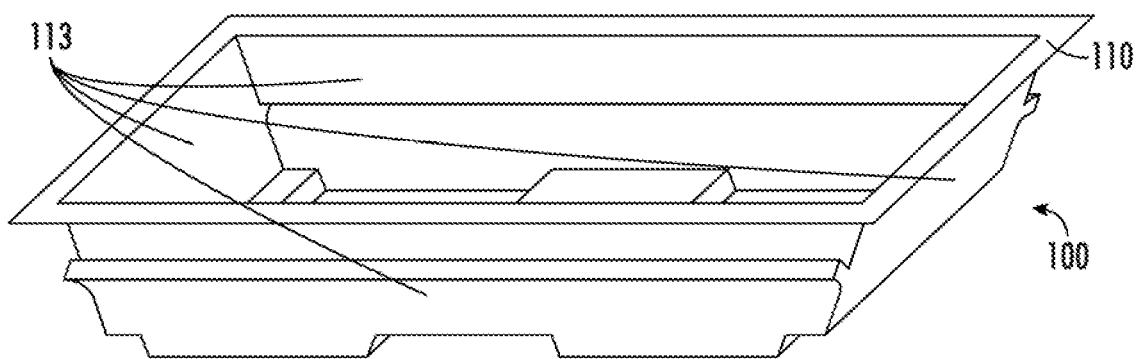
FIG. 2 is another perspective view illustrating an embodiment of the intraoperative sterilization apparatus according to the present invention depicted in FIG. 1.
Figure 3:
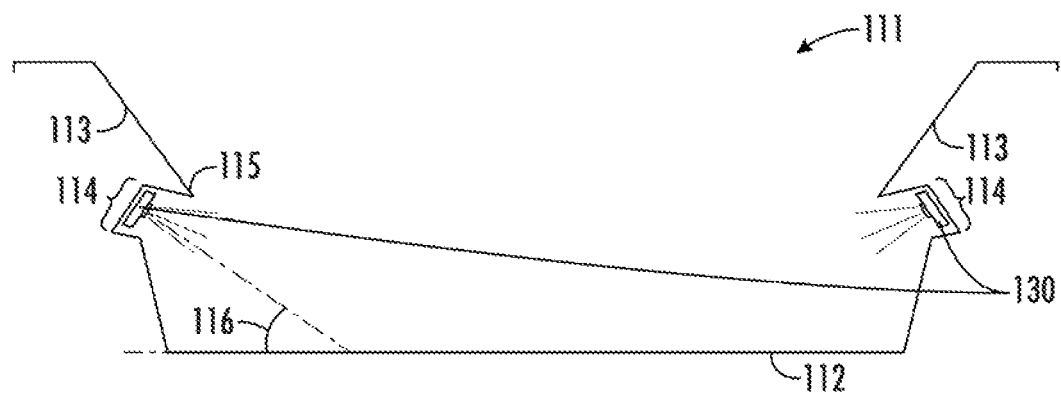
FIG. 3 is a side perspective view illustrating an embodiment of the intraoperative sterilization apparatus according to the present invention depicted in FIGS. 1-2.

FIGS. 1-3 depicts one embodiment of the intraoperative sterilization device 100 according to the present invention comprising a basin or container 110, vibration means 120, radiation means 130, control module 140, and power supply 150 (not shown). Container 110 is configured to have an aperture 111 (for receiving surgical instruments or other items or parts to be cleaned, decontaminated, and/or sterilized), a bottom portion 112, and one or more sidewalls 113 that define an instrument bath for holding a cleaning agent (not shown). Control module 140 is configured to control various components of apparatus 100, including vibration means 120, and radiation means 130. It is contemplated that container 110 can be configured to include additional components to make aperture 111 closeable through various methods known in the art.

It is contemplated that apparatus 100 and/or container 110 can be configured to be disposable for single use applications. But container 110 can also be configured to receive and/or be utilized in conjunction with a separate disposable or reusable liner insert or barrier layer (not shown) that is designed to cover and protect container 110 and/or the other components of apparatus 100 (including vibration means 120, radiation means 130, control module 140, and/or power supply 150 so that they can be reused through known sterilization methods, including steam, ethylene oxide, plasma, gamma, or other sterilization methods). Apparatus 100 and its constituent parts can be configured to be modular such that individual components of apparatus 100 (including container 110, vibration means 120, radiation means 130, control module 140, and/or power supply 150) can be separately disposable and/or reusable through known sterilization methods. Further, apparatus 100 as well as any of its component parts (including container 110, vibration means 120, radiation means 130, control module 140, and/or power supply 150) can be individually or collectively be sterile packaged.

In exemplary embodiments, the cleaning agent comprises an aqueous solution of chlorohexidine. Chlorohexidine concentrations can range from 0.05% to 4%. However, other cleaning, disinfecting, and/or sterilizing are contemplated, including Povidone-iodine (Betadine®), Parachlorometaxylenol, Benzalkonium Chloride, Cocamidopropyl PG-Dimonium Chloride Phosphate, as well as combinations of Chlorohexidine and the aforementioned agents with other antiseptic agents, anti-viral agents, bactericides, microbicides, and/or inert substances, including use of these agents in liquid, solid, morselized, or 25 powdered forms. In one variant (not shown), apparatus 100 and/or container 110 can be prepackaged with a disposable single-use, amount of cleaning agent. In other variants, apparatus 100 and/or container 110 can include a pump assembly (not shown) to introduce, drain and/or circulate the aforementioned cleaning agent.

Container 110 (as well as any disposable liner being used in conjunction therewith) can be constructed out of any suitable materials for cleaning, disinfecting and/or sterilizing instruments including stainless steel, metals, metal alloys, any suitable polymers (including injection-molded polymers, polyethylene terephthalate (PET), high density polyethylene (HDPE), polyvinyl chloride (PVC), low density polyethylene (LDPE), polypropylene (PP), polystyrene, or any other suitable natural/synthetic polymers), carbon fibers and/or any other materials that are capable of being formed, molded, extruded, transformed, forged, and/or cast. In addition, it is contemplated that container 110 (as well as any disposable liner being used in conjunction therewith) can be configured to have any suitable shape, such as e.g. rectangular, square, round, angled, and/or channeled. It is further contemplated that container 110 (as well as any disposable liner being used in conjunction therewith) can have any suitable size and dimensions, but preferably having a length of 18-36 inches, a width of 8-18 inches, and a height of 6-12 inches. It is further contemplated that an interior surface of container 110 (including the interior surface of any disposable liner being used in conjunction therewith) can have a non-reflective surface, including a matte black surface or a matte stainless-steel surface. Bottom 112 of container 110 can also be configured to include one or more features that allow it to mate, fit with, couple with, and/or be attached to, a double O-ring stand (as is used in operating rooms), other operating room equipment, and/or its own moveable base support system (not shown).

Figure 4:
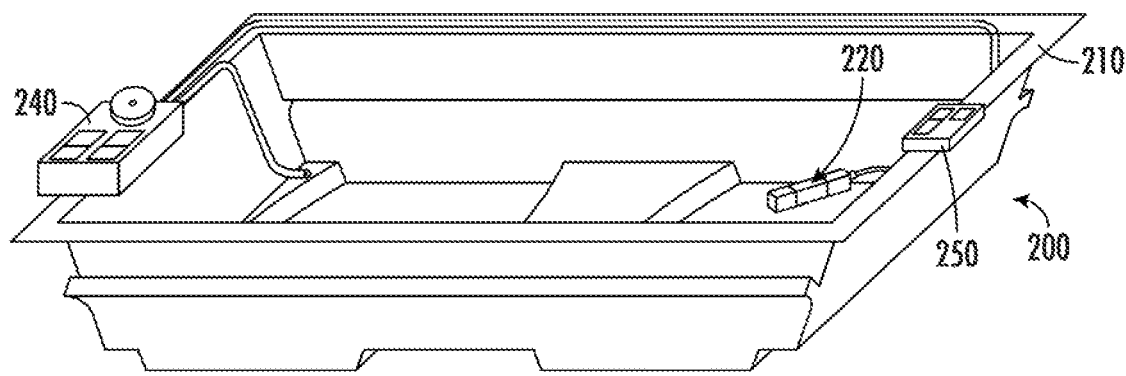
FIG. 4 is a perspective view illustrating another embodiment of the intraoperative sterilization apparatus according to the present invention.
Figure 6:
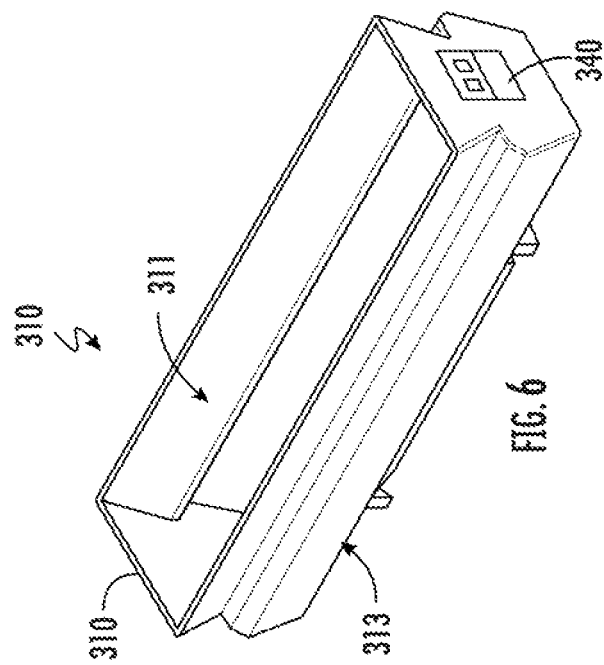
FIG. 6 is a perspective view illustrating an embodiment of the intraoperative sterilization apparatus according to the present invention depicted in FIG. 5.
Figure 8:
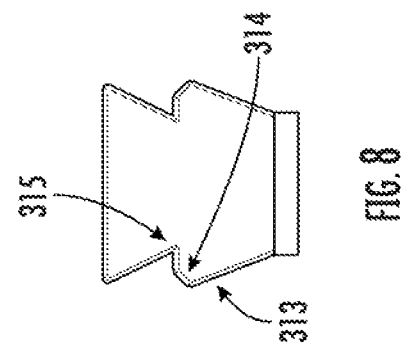
FIG. 8 is a cross-sectional perspective view illustrating an embodiment of the intraoperative sterilization apparatus according to the present invention shown in FIG. 5-7.
Figure 5:
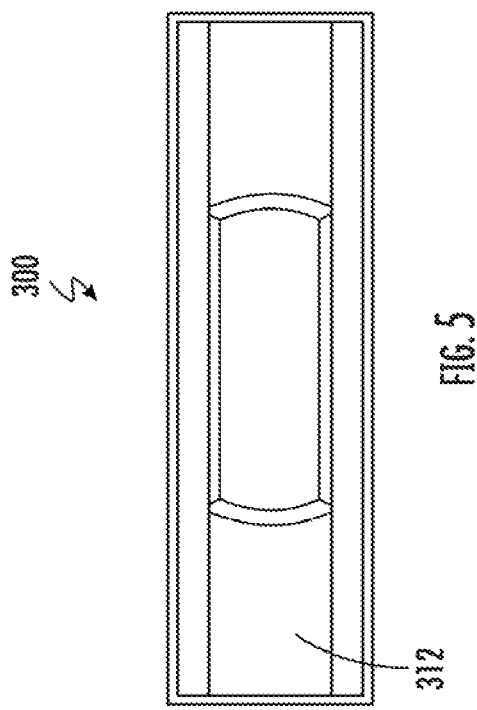
FIG. 5 is a top perspective view illustrating yet another embodiment of the intraoperative sterilization apparatus according to the present invention.
Figure 7:
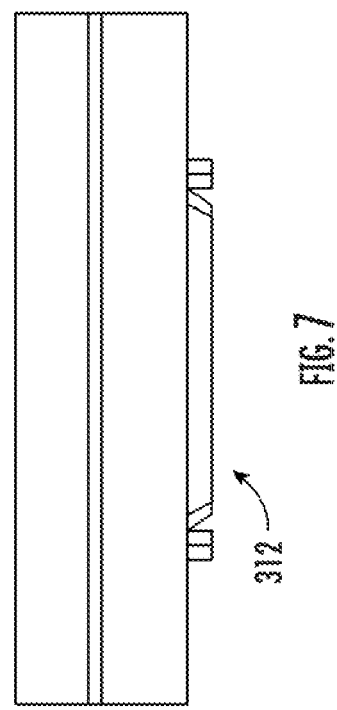
FIG. 7 is a side perspective view illustrating an embodiment of the intraoperative sterilization apparatus according to the present invention depicted in FIG. 5-6.

In exemplary embodiments, vibration means 120 is configured to emit ultrasonic radiation or vibrations for cleaning, disinfecting and/or sterilizing instruments. In one variant, vibration means 120 can be disposed within the bottom of container 110. As shown in FIG. 1, vibration means 120 is depicted as being molded within container 110. In other variants, it is contemplated that vibration means 120 can be a separate modular component (as shown in FIG. 4), as well as being coupled to container 110 in any suitable fashion. Vibration means 120 can further comprise a motor and/or one or more generators or transducers for emitting ultrasonic vibrations or radiation. Vibration means 120 can also be configured to include additional components that allow it to separately agitate, cause movement of, or vibrate container 110 or any other component of apparatus 100. The ultrasonic radiation is contemplated to have a frequency in a range of at least 20 kilohertz to 120 kilohertz, but more preferably in a range of at least 20 kilohertz to 80 kilohertz, and most preferably in a range of 40 kilohertz to 60 kilohertz, but other suitable frequency ranges are contemplated. Still further, it is contemplated that control unit 140 is coupled to vibration means 120 for adjusting the frequency of the ultrasonic radiation, vibrations, or agitation to optimize the cleaning, disinfecting and/or sterilization capability of the apparatus for various applications.

Radiation means 130 is configured to emit UV radiation for cleaning, disinfecting and/or sterilizing instruments. Radiation means 130 can comprise one or more individual UV lights, UV LEDs or strips of UV lights or UV LEDs. It is further contemplated that radiation means 130 is capable of emitting ultraviolet radiation having a wavelength in the range of at least 10 nanometers to 400, but more preferably in the UV-C wavelength range of at least 100 nanometers to 280 nanometers, and more preferably in the UV-C wavelength range of at least 200 nanometers to 230 nanometers. Still further, it is also contemplated that the control module 140 is coupled to radiation means 130 for adjusting the light wavelength and/or exposure duration to optimize the cleaning, disinfecting and/or sterilization capability of the apparatus for various applications.

In one variant, depicted in FIG. 3, apparatus 100 includes radiation means 130 disposed within a longitudinal groove or channel 114 in sidewalls 113, which is configured to protect end users from being exposed to harmful UV light. But channel 114 can be configured to have other appropriate sizes and dimension, including being longitudinal or horizontal slits, wells, and/or depressions. It is further contemplated that radiation means 130 can be shrouded, directed or aimed in any suitable manner as to reduce and/or eliminate human exposure to the radiation source. Radiation means 130 can be disposed in sidewalls 113 in a single row fashion. Further, radiation means 130 can comprise a single light source or multiple rows of light sources in only one sidewall, more than one sidewall, and/or all sidewalls of apparatus 100. Radiation means 130 can be modular and/or reusable light sources. Radiation means 130 can also be disposed within channel 114 in a manner so that light source 130 is sealed to prevent it from being damaged, which includes but is not limited to embedding and sealing light source 130 in channel 114 with a clear resin (not shown) or by sealing channel 114 with a clear plastic cover (not shown).

Still further, in other variants, as depicted in FIG. 3, channel 114 can be configured to include a shrouded lip portion 115 to aid in directing the ultraviolet radiation at the instruments in container 110 and away from the operator. Channel 114 and/or radiation means 130 can be configured to be angled downwards (at an operation angle 116 depicted in FIG. 3) relative to the bottom 112 of container 110 so that radiation means 130 is directed towards the instruments in container 110 and away from the operator. Additionally, operation angle 116 can be configured to direct the radiation being emitted from radiation means 130 just below the bottom of the opposing shrouded lip 115 portion. Operation angle 16 is preferred to be in the range of at least 5-80 degrees, but more preferably in the range of at least between 10-65 degrees, and most preferably in the range of at least 15-50 degrees.

Control module 140 houses electronics for controlling vibration means 120, radiation means 130, as well as any other components of apparatus 100 that are capable of being controlled. In one variant, it is contemplated that the apparatus of the present invention can include a heating assembly (not shown) and temperature controls (not shown) that can be controlled by control module 140. Further, it is contemplated that power supply 150 (not shown) supplies power to control module 140, vibration means 120 and radiation means 130, as well as any other component of apparatus 100 that requires power. Apparatus 100 can be battery powered and/or be used with any other suitable power sources, including rechargeable, or solar powered, cells and/or other AC/DC power sources. Further, control module 140 can mounted, molded within, or coupled to container 110 in any suitable manner, and/or be a handheld unit.

FIG. 4 depicts another embodiment of the intraoperative sterilization device 200 according to the present invention comprising container 210, vibration means 220, radiation means 230 (not shown), control module 140, and power supply 250. Vibration means 220 is configured to be a separate modular unit from container 210 and includes a heating assembly. FIGS. 5-8 depicts yet another embodiment of the intraoperative sterilization apparatus 300 according to the present invention comprising container 310, vibration means 320 (not shown), radiation means 330 (not shown), control module 340, and power supply 350 (not shown). Container 310 includes a slim aperture 311, bottom portion 312, and sidewalls 313 that define an instrument bath for holding a cleaning agent (not shown). Container 310 is depicted as having the control module 340 molded within one of the sidewalls of container 310 and further having the power source (not shown) being integrated within the control module 340 and molded within container 310.

Exemplary Electronic System

Figure 9:
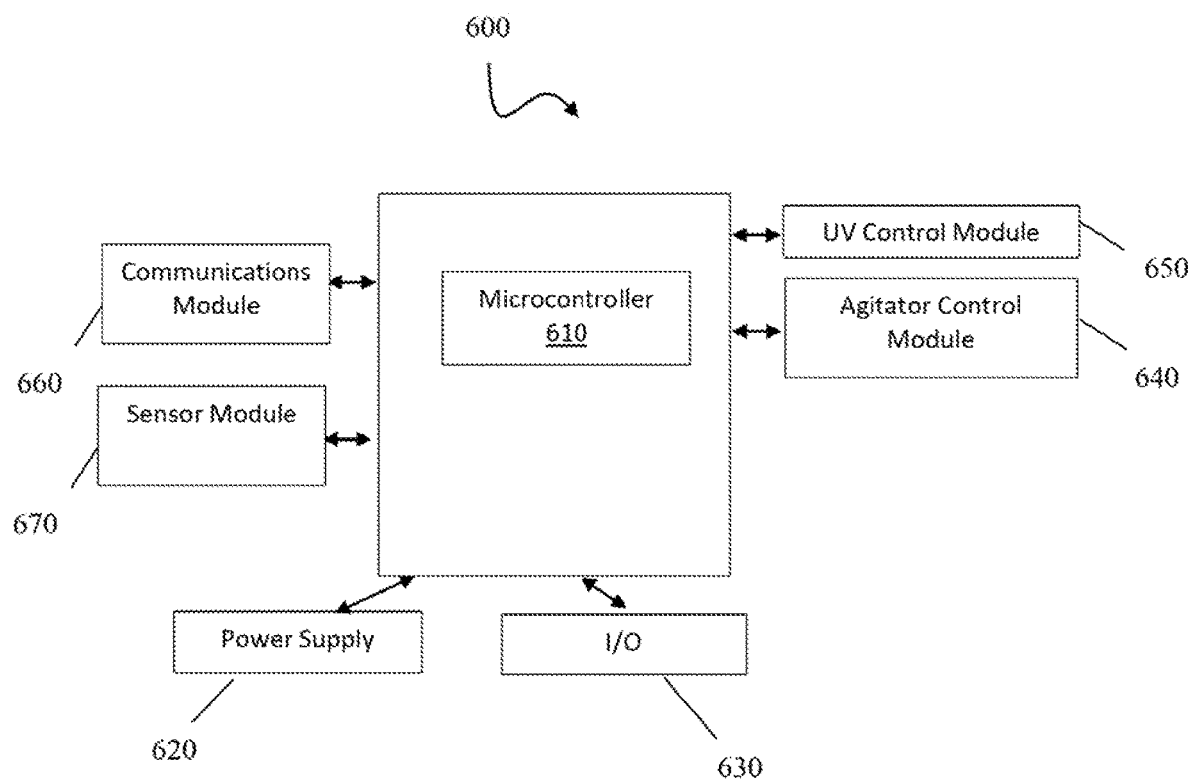
FIG. 9 is a block diagram of an embodiment of an electronic control system useful with the intraoperative sterilization apparatus according to the present invention.

FIG. 9 depicts a functional block diagram of one exemplary embodiment of an electronic subsystem 600 for use with control module 140 of the present invention. One of ordinary skill in the art will appreciate that subsystem 600 may include, without limitation, many additional components not shown, including network components (including location services) to allow the apparatus to function in connection with one or more user devices (such as e.g. mobile phones, smartphones, tablets, wearable devices). Electronic subsystem 600 comprises: microcontroller 610; power supply 620 (which can be configured for wired or battery powered operation); input/output module 630 for connecting various input and/or output devices; vibration/agitator control module 640 configured to control the vibration means; radiation control module 650 for controlling UV light source; communications module 660 (e.g. Wi-Fi, Bluetooth transceivers and network interface controllers (NICs), and GPS); and a sensor module 670 configured to monitor various aspects of the apparatus during operation.

Exemplary Methods

Figure 10:
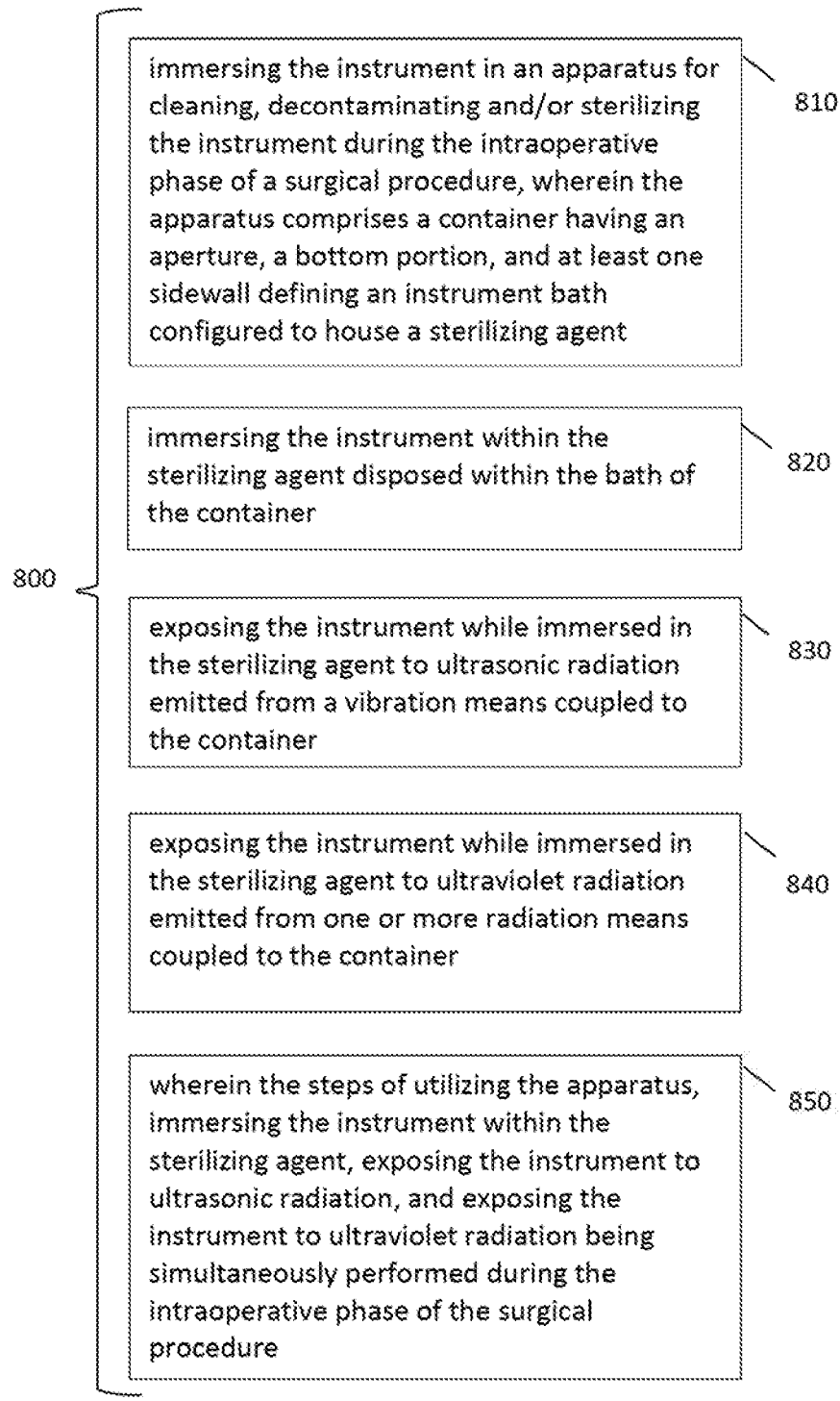
FIG. 10 is a logical flow diagram illustrating the steps of a method of using the intraoperative sterilization apparatus according to the present invention.

FIG. 10 depicts a logical flow diagram illustrating an exemplary method of using the intraoperative sterilization apparatus of the present invention to clean, decontaminate, and/or sterilize an instrument or multiple instruments during the intraoperative phase of a surgical procedure. Step 810, depicts utilizing an apparatus for cleaning, decontaminating and/or sterilizing the instrument during an intraoperative phase of a surgical procedure, wherein the apparatus comprises a container having an aperture, a bottom portion, and at least one sidewall defining an instrument bath configured to house a cleaning agent. It is contemplated that the container can be disposable and/or be utilized in conjunction with a disposable liner inset. Step 820, depicts immersing the instrument within the cleaning agent disposed within the bath of the container. Step 830, depicts exposing the instrument while immersed in the cleaning agent to ultrasonic radiation emitted from a vibration means coupled to the container. Step 840, depicts exposing the instrument while immersed in the cleaning agent to ultraviolet radiation emitted from one or more radiation means coupled to the container. It is contemplated that the vibration means and/or radiation means can be coupled to the container in modular fashion and/or be molded within the container. Step 850, depicts the steps of utilizing the apparatus, immersing the instrument within the cleaning agent, exposing the instrument to ultrasonic radiation, and exposing the instrument to ultraviolet radiation simultaneously being performed during the intraoperative phase of the surgical procedure. Further, it is contemplated that addition embodiments of the apparatus disclosed herein can be incorporated into the foregoing method.

Thus, specific embodiments of apparatus and methods for cleaning, decontaminating, and/or sterilizing an instrument during an intraoperative phase of a surgical procedure have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprising," "comprises," and "comprise" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C, . . . and N, the text should be interpreted as requiring only one element from the group, not A plus N, or B plus N, etc.

What is claimed is:

1. A method for cleaning, decontaminating and/or sterilizing instrument, said method comprising:

immersing said instrument in an apparatus for cleaning, decontaminating and/or sterilizing said instrument during an intraoperative phase of a surgical procedure, said apparatus comprising a container having an aperture, a bottom portion, and at least one sidewall defining a bath configured to hold a cleaning agent;

immersing said instrument within said cleaning agent disposed within said bath of said container;

exposing said instrument while immersed in said cleaning agent to an ultrasonic radiation emitted from a vibration means coupled to said container; and exposing said instrument while immersed in said cleaning agent ultraviolet radiation emitted from one or more radiation means coupled to said container;

wherein said steps of immersing said instrument within said cleaning agent, exposing said instrument to ultrasonic radiation, and exposing said instrument to ultraviolet radiation are simultaneously performed during said intraoperative phase of said surgical procedure; and wherein said at least one sidewall further comprises a longitudinal channel disposed within said at least one sidewall, wherein said longitudinal channel within said at least one sidewall is configured to have an operational angle of between 15 to 50 degrees relative to said bottom portion of said container, and wherein said radiation means is disposed within said longitudinal channel, and wherein said longitudinal channel further comprises a shrouded lip portion.

2. The method of claim 1, wherein the apparatus for cleaning, decontaminating, and/or sterilizing said instrument during said intraoperative phase of said surgical procedure, further comprises a power supply.

3. The method of claim 1, wherein said apparatus for cleaning, decontaminating, and/or sterilizing said instrument during said intraoperative phase of said surgical procedure, is disposable and comprises modular components.

4. The method of claim 1, wherein interior surfaces of said container further comprise a non-reflective surface.

5. The method of claim 1, wherein said apparatus for cleaning, decontaminating, and/or sterilizing said instrument during said intraoperative phase of said surgical procedure, further comprises a pump assembly.

6. The method of claim 1, wherein said cleaning agent comprises an aqueous solution of chlorohexidine.

7. The method of claim 1, wherein said radiation means is configured to emit ultraviolet radiation in a range of at least 100 nanometers to 400 nanometers.

8. The method of claim 1, wherein said vibration means is configured to emit ultrasonic radiation in a range of at least 20 kilohertz to 120 kilohertz.

9. The method of claim 1, wherein said apparatus further comprises a control module.

10. The method of claim 1, wherein said apparatus further comprises a heating assembly.

11. The method of claim 1, wherein said apparatus is battery powered.

12. The method of claim 1, wherein said container is further configured to receive a disposable liner insert.

13. The method of claim 1, wherein said cleaning agent is prepackaged with said container in disposable fashion.

14. A method for cleaning, decontaminating, and/or sterilizing an instrument, said method comprising:

immersing said instrument in an apparatus for cleaning, decontaminating and/or sterilizing said instrument during an intraoperative phase of a surgical procedure, said apparatus comprising a container having an aperture, a bottom portion, and at least one sidewall defining a bath configured to hold a cleaning agent, and wherein said container further comprises a disposable liner insert;

immersing said instrument within said cleaning agent disposed within said bath of said container;

exposing said instrument while immersed in said cleaning agent to an ultrasonic radiation emitted from a vibration means coupled to said container; and exposing said instrument while immersed in said cleaning agent to ultraviolet radiation emitted from one or more radiation means coupled to said container;

wherein said steps of immersing said instrument within said cleaning agent, exposing said instrument to ultrasonic radiation, and exposing said instrument to ultraviolet radiation are simultaneously performed during said intraoperative phase of said surgical procedure; and wherein said at least one sidewall further comprises a longitudinal channel disposed within said at least one sidewall and configured to have an operational angle of between 15 to 50 degrees relative to said bottom portion, and wherein said radiation means is disposed within said longitudinal channel, and wherein said longitudinal channel further comprises a shrouded lip portion.

15. The method of claim 14, wherein said vibration means and said radiation means are molded within said container.

16. The method of claim 15, wherein said cleaning agent comprises an aqueous solution of chlorohexidine, said radiation means is configured to emit ultraviolet radiation in a range of at least 100 nanometers to 400 nanometers, and said vibration means is configured to emit ultrasonic radiation in a range of at least 20 kilohertz to 120 kilohertz.

* * * * *